United States Patent [19]
Baker et al.

[11] Patent Number: 5,919,781
[45] Date of Patent: Jul. 6, 1999

[54] USE OF NK-1 RECEPTOR ANTOGONISTS FOR TREATING SUBSTANCE USE DISORDERS

[75] Inventors: Raymond Baker, Dursley; Neil Roy Curtis, Puckeridge; Jason Matthew Elliott, Felsted; Timothy Harrison, Great Dunmow; Gregory John Hollingworth, Basildon; Philip Stephen Jackson, Harlow; Janusz Jozef Kulagowski, Sawbridgeworth; Nadia Melanie Rupniak; Eileen Mary Seward, both of Bishops Stortford; Christopher John Swain, Duxford; Brian John Williams, Great Dunmow, all of United Kingdom

[73] Assignee: Merck Sharp & Dohme Ltd., Hoddesdon, United Kingdom

[21] Appl. No.: 08/980,927

[22] Filed: Dec. 1, 1997

[30] Foreign Application Priority Data

| Dec. 2, 1996 | [GB] | United Kingdom | 9625051 |
| Jan. 24, 1997 | [GB] | United Kingdom | 9701459 |
| Jun. 27, 1997 | [GB] | United Kingdom | 9713715 |
| Aug. 12, 1997 | [GB] | United Kingdom | 9717097 |

[51] Int. Cl.[6] .................... A61K 31/535; A61K 31/445
[52] U.S. Cl. ...................... 514/236.2; 514/237.8; 514/315; 514/810; 514/811; 514/812; 514/813
[58] Field of Search ................ 514/236.2, 237.8, 514/315, 810, 811, 812, 813

[56] References Cited

U.S. PATENT DOCUMENTS

| 5,162,339 | 11/1992 | Lowe, III | 514/305 |
| 5,496,833 | 3/1996 | Baker et al. | 514/326 |
| 5,538,982 | 7/1996 | Hagan et al. | 514/305 |
| 5,612,337 | 3/1997 | Baker et al. | 514/236.2 |
| 5,719,147 | 2/1998 | Dorn et al. | 514/227.5 |
| 5,728,695 | 3/1998 | Harrison et al. | 514/230.8 |

FOREIGN PATENT DOCUMENTS

| 0 577 394 | 1/1994 | European Pat. Off. . |
| WO 94/20500 | 9/1994 | WIPO . |
| WO 95/08549 | 3/1995 | WIPO . |
| WO 95/18124 | 7/1995 | WIPO . |
| WO 96/05181 | 2/1996 | WIPO . |
| WO 96/24353 | 8/1996 | WIPO . |

OTHER PUBLICATIONS

Aguiar, M., et al., *Physiology & Behavior*, 1996, 60(4) 1183–1186.
Barden, N., et al., *J. Neurochem.*, 1983, 41, 834–840.
Brodin, E., et al., *Neuropharmacology*, 1987, 26(6) 581–590.
Brodin, E., et al., *Neuropeptides*, 1994, 26, 253–260.
Culman, J., et al., *J. Physiol. Pharmacol.*, 1995, 73, 885–891.
Cutler, et al., *J. Psychopharmacol*, 1994, 8, A22, 87.
Elliott, P.J., *Exp. Brain Res. UK*, 1988, 73, 354–356.
F–D–C Reports—Prescription Pharmaceuticals and Biotechnology, Dec. 8, 1997, 59 (49), 10.
File, S.E., *Pharm. Biochem. Behavior*, 1997, 58, 3, 747–752.
Kramer, et al., *Science*, 1998, 281, 1640–1645.
Lowe, J., et al., *Drug News Perspect*, 1992, 5 (4), 223.
Malek–Ahmadi, Neuroscience and Behavioral Reviews, 1992, 16, 365–359.
Rimon, R., et al., *Biological Psychiatry*, 1984, 19(4), 509–516.
Roccon, et al., *Pharmacological Research*, 1995, 31, 191.
Shaikh, M., et al., *Brain Research*, 1993, 625, 283–294.
Shirayama, Y., et al., *Brain Research*, 1996, 739, 70–78.
Siegel, R., et al., *Neurochem. Int.*, 1984, 6(6), 783–789.
Siegel, A., et al., *Aggressive Behavior*, 1995, 21, 49–62.
Teixeira, R., et al., *European J. Pharm.*, 1996, 311, 7–14.
Vassout, et al., *Neuropeptides*, 1994, 26 (Suppl. 1), 38.
Wahlestedt *Science*, 1998, 281, 1624–1625.
*Wall Street Journal*, Aug. 13, 1998, B1, Col. 2.
CA 120:69382, McLean et al., 1993.

*Primary Examiner*—Kimberly Jordan
*Attorney, Agent, or Firm*—J. Eric Thies; David L. Rose

[57] ABSTRACT

The present invention provides a method for the treatment or prevention of substance use disorders using an orally active, long acting, CNS-penetrant NK-1 receptor antagonist and pharmaceutical compositions comprising such a NK-1 receptor antagonist.

6 Claims, No Drawings

USE OF NK-1 RECEPTOR ANTAGONISTS FOR TREATING SUBSTANCE USE DISORDERS

CROSS REFERENCE TO RELATED APPLICATIONS

This application claims priority under 35 U.S.C. §119(a) from Great Britain Application No. 9625051.9, filed Dec. 2, 1996, Great Britain Application No. 9701459.1, filed Jan. 24, 1997, Great Britain Application No. 9713715.2, filed Jun. 27, 1997, and Great Britain Application No. 9717097.1, filed Aug. 12, 1997

This invention relates to the treatment or prevention of certain substance use disorders by the administration of a specific class of NK-1 receptor antagonists.

A common, though not inevitable, outcome of long-term drug use is the occurrence of a withdrawal response, which occurs either when the drug is withdrawn or when an antagonist is given and which usually takes the form of some sort of adverse reaction.

A withdrawal syndrome occurs in opiate addicts when the opiate is withdrawn or when an antagonist, such as naloxone, is given. The symptoms consist of yawning, rhinorrhoea, and sweating, followed by the so-called cold turkey, in which there is shivering and goose flesh. Later, nausea, vomiting, diarrhoea, and hypertension may occur. The acute syndrome subsides within a week, but the addict may have anxiety and sleep disturbances for several weeks or months after. This syndrome can be avoided by introducing increasing doses of methadone as the opiate is withdrawn, as the later withdrawal of methadone, which has a much longer duration of action than morphine, may not result in this syndrome.

Delirium tremens may occur on withdrawal of alcohol from chronic alcoholics. This syndrome consists of disorientation and visual hallucinations.

Withdrawal of benzodiazepines after long-term therapy may result in a disturbance of sleep pattern (rebound insomnia assicated with abnormal sleep patterns), agitation, restlessness, and occasionally epileptic convulsions.

The pharmacological management of drug withdrawal disorders is not always effective and is often hampered by the addictive potential of many of the drugs which are prescribed to treat withdrawal symptoms.

Neurokinin 1 (NK-1; substance P) receptor antagonists are being developed for the treatment of a number of physiological disorders associated with an excess or imbalance of tachykinins, and in particular substance P. Examples of conditions in which substance P has been implicated include disorders of the central nervous system such as anxiety, depression and psychosis (see, for instance, International (PCT) patent specification Nos. WO 95/16679, WO 95/18124 and WO 95/23798).

More recently, International (PCT) patent specification No. WO 96/24353 (published Aug. 15, 1996) suggests that a more efficacious and safe treatment of psychiatric disorders would be achieved using a combination of a tachykinin antagonist and a serotonin agonist or selective serotonin reuptake inhibitor (SSRI). However, such a regimen would not be free of side-effects due to the serotonin agonist or SSRI.

It has been reported that central (i.c.v.) injection of RP67580 could attenuate naloxone-precipitated withdrawal signs in rats receiving morphine for five days (Maldonado et al, *Neurosci. Letts.*, 156: 135, 1993). This study resembles an earlier report using guinea-pigs showing that the morphine withdrawal response was inhibited by i.c.v. injection of peptide substance P antagonists (Johnston & Chahl, *Arch. Pharmacol.*, 343: 283, 1991). These investigators subsequently attempted to block the withdrawal response in guinea-pigs using systemic administration of CP-96,345, and found that only high doses (20 mg/kg) were active, and this could therefore not be attributed with confidence to a specific blockage of NK-1 receptors (Chahl & Johnston, *Regul. Pept. Suppl.* 1, S43, 1992).

NK-1 receptor antagonists are described in published European Patent Specification Nos. 0 360 390, 0 394 989, 0 429 366, 0 443 132, 0 482 539, 0 512 901, 0 512 902, 0 514 273, 0 514 275, 0 517 589, 0 520 555, 0 522 808, 0 528 495, 0 532 456, 0 533 280, 0 536 817, 0 545 478, 0 577 394, 0 590 152, 0 599 538, 0 610 793, 0 634 402, 0 686 629, 0 693 489, 0 694 535, 0 699 655, 0 699 674, 0 707 006, 0 708 101, 0 714 891, 0 723 959, 0 733 632 and 0 776 893; and in International Patent Specification Nos. 90/05525, 90/05729, 91/09844, 91/18899, 92/01688, 92/06079, 92/12151, 92/15585, 92/17449, 92/20661, 92/20676, 92/21677, 93/00330, 93/00331, 93/01159, 93/01165, 93/01169, 93/01170, 93/06099, 93/09116, 93/10073, 93/14113, 93/18023, 93/19064, 93/21155, 9321181, 93/23380, 93/24465, 94/01402, 94/02461, 94/03429, 94/03445, 94/04494, 94/04496, 94/05625, 94/07843, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 96/22525, 95/23798, 95/26338, 95/28418, 95/30674, 95/30687, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British-Patent Specification Nos. 2 266 529, 2 268 931, 2 269 170, 2 269 590, 2 271 774, 2 292 144, 2 293 168, 2 293 169, and 2 302 689.

In view of the short-comings of existing therapy for substance use disorders, there is a need for new, safe and effective treatment for such disorders.

The present invention provides the use of a CNS penetrant NK-1 receptor antagonist in an oral, once-a-day medicament for the treatment of substance use disorders. The compounds of this class advantageously exhibit a rapid onset of action and a reduced side-effect profile when compared against conventional therapy.

In particular, the present invention provides a means for the identification of NK-1 receptor antagonists which would be effective in an oral once-a-day medicament for the treatment of substance use disorders. The aforementioned patent specifications which describe NK-1 receptor antagonists provide no reliable method for the identification of such compounds.

The exceptional pharmacology of the class of NK-1 receptor antagonists of use in the present invention enables the treatment of substance use disorders, without the need for concomitant therapy.

Furthermore, the exceptional pharmacology of the class of NK-1 receptor antagonists of use in the present invention results in a rapid onset of action.

The present invention accordingly provides the use of an orally active, long acting, CNS-penetrant NK-1 receptor antagonist (as hereinafter defined) for the manufacture of a medicament adapted for oral administration for the treatment or prevention of substance use disorders.

The present invention also provides a method for the treatment or prevention of substance use disorders, which method comprises the oral administration to a patient in need of such treatment of an effective amount of an orally active, long acting, CNS-penetrant NK-1 receptor antagonist (as hereinafter defined).

In a further aspect of the present invention, there is provided an oral pharmaceutical composition for the treatment of substance use disorders which comprises an orally active, long acting, CNS-penetrant NK-1 receptor antagonist (as hereinafter defined), together with a pharmaceutically acceptable carrier or excipient.

As used herein, the term "substance use disorders" includes substance dependence or abuse with or without physiological dependence. The substances associated with these disorders are: alcohol, amphetamines (or amphetamine-like substances), caffeine, cannabis, cocaine, hallucinogens, inhalants, nicotine, opioids, phencyclidine (or phencyclidine-like compounds), sedative-hypnotics or benzodiazepines, and other (or unknown) substances and combinations of all of the above.

In particular, the term "substance use disorders" includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation.

Other "substance use disorders" include substance-induced anxiety disorder with onset during withdrawal; substance-induced mood disorder with onset during withdrawal; and substance-induced sleep disorder with onset during withdrawal.

As used herein, the term "treatment" refers both to the prevention and/or acute and maintenance treatment of the aforementioned conditions.

Preferred NK-1 receptor antagonists for use in the present invention are selected from the classes of compounds described in European Patent Specification No. 0 577 394, and International Patent Specification Nos. 95/08549, 95/18124, 95/23798 and 96/05181, and International Patent Application No. PCT/GB97/01630. The preparation of such compounds is fully described in the aforementioned publications.

Particularly preferred NK-1 receptor antagonists of use in the present invention include:

2-(S)-(3,5-bis(trifluoromethyl)benzyloxy)-3-(S)-(4-fluorophenyl)-4-(3-(5-oxo-1H,4H-1,2,4-triazolo) methyl)morpholine;

2-(R)-(1-(R)-(3,5-bis(trifluoromethyl)phenyl)ethoxy)-4-(3-(5-oxo-1H,4H-1,2,4-triazolo)methyl)-3-(S)-phenyl-morpholine;

2-(S)-(3,5-bis(trifluoromethyl)benzyloxy)-4-(3-(5-oxo-1H,4H-1,2,4-triazolo)methyl)-3-(S)-phenyl-morpholine;

2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine;

2-(R)-(1-(R)-(3,5-bis(trifluoromethyl)phenyl)ethoxy)-4-(5-(N,N-dimethylamino)methyl-1,2,3-triazol-4-yl) methyl-3-(S)-phenylmorpholine;

2-(R)-(1-(R)-(3,5-bis(trifluoromethyl)phenyl)ethoxy)-4-(5-(N,N-dimethylamino)methyl-1,2,3-triazol-4-yl) methyl-3-(S)-(4-fluorophenyl)morpholine;

2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine;

2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine;

2-(R)-(1-(R)-(3,5-bis(trifluoromethyl)phenyl)ethoxy)-4-(4-N,N-dimethylaminobut-2-yn-yl)-3-(S)-(4-fluorophenyl)morpholine;

(3S,5R,6S)-3-[2-cyclopropoxy-5-(trifluoromethoxy) phenyl-1-oxa-7-aza-spiro[4.5]decane;

(3R,5R,6S)-3-[2-cyclopropoxy-5-(trifluoromethoxy) phenyl-1-oxa-7-aza-spiro[4.5]decane;

or a pharmaceutically acceptable salt thereof.

Full descriptions of the preparation of the NK-1 receptor antagonists which may be employed in the present invention may be found in the references cited herein.

Suitable pharmaceutically acceptable salts of the NK-1 receptor antagonists of use in the present invention include acid addition salts which may, for example, be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, phosphoric acid or sulphuric acid. Salts of amine groups may also comprise the quaternary ammonium salts in which the amino nitrogen atom carries an alkyl, alkenyl, alkynyl or aralkyl group. Where the compound carries an acidic group, for example a carboxylic acid group, the present invention also contemplates salts thereof, preferably non-toxic pharmaceutically acceptable salts thereof, such as the sodium, potassium and calcium salts thereof.

Preferably the compositions containing an NK-1 receptor antagonist of use according to the present invention are in unit dosage forms such as tablets, pills, capsules, wafers and the like. Additionally, the NK-1 receptor antagonists of use according to the present invention may be presented as granules or powders for extemporaneous formulation as volume defined solutions or suspensions. Alternatively, the NK-1 receptor antagonists of use according to the present invention may be presented in ready-prepared volume defined solutions or suspensions. Preferred forms are tablets and capsules.

For preparing solid compositions such as tablets, the principal active ingredient is mixed with a pharmaceutical carrier, e.g. conventional tableting ingredients such as corn starch, lactose sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil, peanut oil or soybean oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions of the present invention may also be administered via the buccal cavity using conventional technology, for example, absorption wafers.

Compositions in the form of tablets, pills, capsules or wafers for oral administration are particularly preferred.

A minimum dosage level for the NK-1 receptor antagonist is about 5 mg per day, preferably about 10 mg per day and especially about 20 mg per day. A maximum dosage level for the NK-1 receptor antagonist is about 1500 mg per day, preferably about 1000 mg per day and especially about 500 mg per day. The compounds are administered once a day.

It will be appreciated that the amount of the NK-1 receptor antagonist required for use in the treatment or prevention of substance use disorders will vary not only with the particular compounds or compositions selected but also with the route of administration, the nature of the condition being treated, and the age and condition of the patient, and will ultimately be at the discretion of the patient's physician or pharmacist.

Two compounds of use in the present invention which are described in International Patent Application No. PCT/GB97/01630 may be prepared according to the following methods:

PREPARATION 1
(2S)-1-tert-Butoxycarbonyl-2-phenylpiperidin-3-one

Dimethyl sulfoxide (20.80 ml, 22.90 g, 29.3 mmol) in dichloromethane (75 ml) was added dropwise to a cooled (−70° C.) solution of oxalyl chloride (13.95 ml, 20.30 g, 160 mmol) in dichloromethane (350 ml). The mixture was stirred at −70° C. for 15 minutes, then (2S,3S)-1-tert-butoxycarbonyl-3-hydroxy-2-phenylpiperidine (prepared by the method described in European Patent Specification number 0 528 495-A; 36.91 g, 133 mmol) in dichloromethane (150 ml) was added dropwise. The mixture was stirred at −70° C. for 20 minutes, then allowed to warm to −30° C. The mixture was cooled to −50° C. and triethylamine (55.95 ml, 40.45 g, 400 mmol) was added slowly. The mixture was allowed to warm to 0° C. and diluted with ice-cooled dichloromethane (250 ml). The mixture was washed with ice cold aqueous citric acid solution (5%, 2×300 ml) and water (300 ml), dried (MgSO$_4$), and the solvent was evaporated under reduced pressure to give the title compound as a yellow oil (42.3 g), which was used immediately without further purification. $^1$H NMR (250 MHz, CDCl$_3$) δ 7.5–7.3 (5H, m), 5.8 (1H, br s), 4.2 (1H, br s), 3.4 (1H, m), 2.6 (2H, m), 2.0 (2H, m), and 1.54 (9H, s).

PREPARATION 2
(2S,3R)-1-tert-Butoxycarbonyl-3-hydroxy-3-(2-methylene-3-phenoxypropyl)-2-phenylpiperidine A solution of 3-(chloromagnesio)-2-(phenoxymethyl)-1-propene in THF (0.91M, 3 ml) (Louw et. al., Tetrahedron, 48, 6087–6104, 1992, prepared from 2.74 mmol of 3-chloro-2-(phenoxymethyl)-1-propene) was slowly added to a solution of (2S)-1-tert-butoxycarbonyl-2-phenylpiperidin-3-one (Preparation 1) in THF (3 ml). The mixture was stirred at room temperature for 1 hours, then saturated aqueous ammonium chloride (20 ml) was added and the mixture was extracted with ethyl acetate (20 ml). The organic phase was washed with brine, dried (MgSO$_4$) and the solvent was evaporated under reduced pressure. The residue was purified by column chromatography on silica gel, eluting with hexane/ethyl acetate (100:0 increasing to 80:20) to give the title compound. $^1$H NMR (360 MHz, CDCl$_3$) δ 7.48 (2H, d, J=6.9 Hz), 7.35–7.2 (6H, m), 6.9–6.88 (3H, m), 5.4 (1H, s), 5.15 (2H, d, J=13.7 Hz), 4.61 (2H, s), 4.11 (2H, m), 3.17 (1H, m), 2.66 and 2.59 (2H, AB d, J=14.0 Hz), 1.95 (2H, m), 1.79 (2H, m), and 1.36 (9H, s). m/z (ES$^+$) 424 (M+1).

PREPARATION 3
(5R,6S)-3-Methylene-6-phenyl-1-oxa-7-(tert-butoxycarbonyl)aza-spiro[4.5]decane To a cooled (−80° C.) solution of (2S,3R)-1-tert-butoxycarbonyl-3-hydroxy-3-(2-methylene-3-phenoxypropyl)-2-phenylpiperidine (Preparation 2, 1.53 g, 3.62 mmol) in THF (20 ml) was added n-butyl lithium (2.5M in hexanes, 1.45 ml, 3.62 mmol) followed by a solution of zinc chloride (0.5M in THF, 7.24 ml, 3.62 mmol). The solution was allowed to warm to room temperature and tetrakis(triphenylphosphine)palladium (0) (0.23 g, 0.2 mmol) was added. The mixture was degassed with bubbling nitrogen and heated under reflux for 16 hours. The mixture was cooled and the solvent was evaporated under reduced pressure. The residue was partitioned between ethyl acetate and 2M sodium hydroxide. The organic phase was washed with saturated brine, dried (MgSO$_4$) and purified by chromatography on a column containing silica gel (eluting with hexane containing increasing proportions of ethyl acetate between 0% to 5%). Evaporation of the fractions gave (6S,5R)-3-methylene-6-phenyl-1-oxa-7-(tert-butoxycarbonyl)aza-spiro[4.5]decane. $^1$H NMR (360 MHz, CDCl$_3$) δ 7.58 (2H, d, J=8.4 Hz), 7.32–7.21 (3H, m), 5.23 (1H, s), 5.06 (1H, m), 4.97 (1H, m), 4.39 (2H, AB d, J=13.3 Hz), 3.99 (1H, dd, J=13.3, 4.48 Hz), 2. 83 (1H, ABd J=15.5 Hz), 2.7 (1H,td J=12.5, 3.93 Hz), 2.5 (1H, ABd, J=15.4 Hz), 2.15 (2H, td, J=12., 0.4 Hz), 1.69 (2H, m), and 1.46 (9H,s). m/z (ES$^+$) 329 (M+2H-$^t$BuOCO).

PREPARATION 4
(5R,6S)-3-Keto-6-phenyl-1-oxa-7-(tert-butoxycarbonyl)aza-spiro[4.5]decane Through a cooled (−80° C.) solution of (5R,6S)-3-methylene-6-phenyl-1-oxa-7-(tert-butoxycarbonyl)aza-spiro[4.5]decane (Preparation 3; 0.665 g) in dichloromethane (5 ml) and methanol (5 ml) was bubbled a mixture of ozone and oxygen for 45 minutes. After the solution had been purged with nitrogen, dimethyl sulphide (0.5 ml) was added and then stirred under nitrogen at room temperature for 16 hours. The solvent was removed in vacuo and the residue partitioned between ethyl acetate and water. The organic phase was dried (MgSO$_4$), evaporated and the residue purified by chromatography on a column containing silica gel (eluting with hexane containing increasing proportions of ethyl acetate between 0% to 10%). Evaporation of the fractions gave the title compound. $^1$H NMR (250 MHz, CDCl$_3$) δ 7.58 (2H, d, J=6.2 Hz), 7.37–7.26 (3H, m), 5.3 (1H, s), 4.15 and 4.09 (2H, AB d, J=17.4 Hz), 3.97 (1H, m), 2.80 (1H, td, J=12.9, 4.0 Hz), 2.74 and 2.48 (2H, ABd, J=18.1 Hz), 2.29 (2H, m), 1.88–1.63 (2H, m), and 1.44 (9H, s). m/z (ES$^+$) 332 (M+1).

PREPARATION 5

(5R,6S)-3-Trifluoromethylsulfonyloxy-6-phenyl-1-oxa-7-(tert-butoxycarbonyl)aza-spiro[4.5]dec-3-ene To a cooled (−80° C.) solution of 1M sodium hexamethyldisilazide (0.38 ml, 0.38 mmol) in THF was added a solution of (5R,6S)-3-keto-6-phenyl-1-oxa-7-(tert-butoxycarbonyl)aza-spiro[4.5]decane (Preparation 4; 0.105 mg, 0.319 mmol) in THF (3 ml). The solution was stirred for 1 hours at −80° C. then a solution of 2-[N,N-bis(trifluoromethylsulfonyl)amino]-5-chloropyridine (0.163 g, 0.415 mmol) in THF (3 ml) was added. The solution was stirred at −80° C. for 30 minutes then at room temperature for 30 minutes before being quenched by addition of saturated ammonium chloride solution and ethyl acetate. The dried (MgSO$_4$) organic phase was purified by chromatography on a column containing silica gel (eluting with hexane containing increasing proportions of ethyl acetate between 0% to 5%). Evaporation of the fractions gave the title compound. $^1$H NMR (360 MHz, CDCl$_3$) δ 7.4 (2H, d, J=7.3 Hz), 7.3–7.22 (3H, m), 6.01 (1H, t, J=2.13 Hz), 5.13 (1H, s), 4.56 and 4.26 (2H, ABdd, J=12.4, 1.97 Hz), 4.10 (1H, dt, J=12.6, 4.22 Hz), 3.00 (1H, m), 2.28–2.04 (2H, m), 1.88–1.76 (2H, m), and 1.37 (9H, s). m/z (ES$^+$) 464 (M+1).

PREPARATION 6

(5R,6S)-3-Trimethylstannyl-6-phenyl-1-oxa-7-(tert-butoxycarbonyl)aza-spiro[4.5]dec-3-ene To a degassed solution of (5R,6S)-3-trifluoromethylsulfonyloxy-6-phenyl-1-oxa-7-(tert-butoxycarbonyl)aza-spiro[4.5]dec-3-ene (Preparation 5; 0.482 g, 1.04 mmol), lithium chloride (0.264 g, 6.25 mmol), lithium carbonate (0.076 g) and hexamethyl distannane (0.96 g, 2.9 mmol) in THF (10 ml) was added triphenylphosphine palladium (0) (0.06 g). The solution was degassed and then heated at 60° C. for 5 hours under nitrogen. Water (20 ml) and ethyl acetate (20 ml) were added and the dried organic phase was purified by chromatography on a column containing silica gel (eluting with hexane containing increasing proportions of ethyl acetate between 0% to 5%). Evaporation of the fractions gave the title compound as a crystalline solid. $^1$H NMR (360 MHz, CDCl$_3$) δ 7.25 (2H, d, J=7.3 Hz), 7.1–7.0 (3H, m), 5.83 (1H, t, J=2.5 Hz), 4.78 (1H, s), 4.48 and 4.02 (2H, dd, J=12.9, 2.3 Hz), 3.96 (1H, dd, J=6.16, 13.4 Hz), 2.95 (1H, td, J=13.3, 4.5 Hz), 1.84 (1H, m), 1.68 (1H, m), 1.60 (2H, m), 1.19 (9H, s), and 0.0 (6H, s).

PREPARATION 7

(2S,3R)-1-tert-Butoxycarbonyl-3-(3-hydroxypropyn-1-yl)-2-phenylpiperidin-3-ol

O-Trimethylsilylpropargyl alcohol (24.51 ml, 20.47 g, 160 ml) was added slowly to a cooled (−10° C.) solution of ethylmagnesium bromide (1M in tetrahydrofuran, 160 ml, 160 mmol). The mixture was stirred at 0° C. for 20 minutes, then at room temperature for 2 hours. The mixture was cooled to −10° C. and a solution of (2S)-1-tert-butoxycarbonyl-2-phenylpiperidin-3-one (Preparation 1; 42.3 g) in tetrahydrofuran (200 ml) was added dropwise over 30 minutes. (Internal temperature below −5° C.). The mixture was stirred at room temperature for 14 hours, poured into water (300 ml) and saturated aqueous ammonium chloride (300 ml) and extracted with ethyl acetate (2×300 ml). The combined organic fractions were washed with brine (300 ml), dried (MgSO$_4$) and the solvent was evaporated under reduced pressure. The residue was dissolved in ethyl acetate (500 ml) and a solution of tetrabutylammonium fluoride (1M in THF, 160 ml, 160 mmol) was added dropwise. The mixture was stirred at room temperature for 30 minutes, water (300 ml) was added, and the layers were separated. The aqueous layer was extracted with ethyl acetate (2×300 ml) and the combined organic fractions were washed with water (300 ml) and brine (300 ml), dried (MgSO$_4$) and the solvent was evaporated under reduced pressure to give the crude title compound as an orange oil (45 g). The crude material was purified by flash column chromatography on silica gel, eluting with hexane/ethyl acetate (90:10 increasing to 25:75) to give the title compound as an amber oil (32.2 g). $^1$H NMR (CDCl$_3$) δ 7.53–7.55 (2H, m), 7.19–7.35 (3H, m), 5.56 (1H, s), 4.27 (2H, s), 3.99–4.03 (1H, m), 3.25 (1H, br s), 2.77–2.81 (1H, m), 2.77 (1H, br s), 2.12–2.20 (1H, m), 1.91–1.99 (2H, m), 1.77–1.83 (1H, m), and 1.39 (9H, s).

PREPARATION 8

2-Bromo-4-(trifluoromethoxy)phenol

To a cooled (0° C.) solution of 4-trifluoromethoxyphenol (35.6 g, 0.2 mol) in chloroform (280 ml) was added dropwise a solution of bromine (32 g, 0.2 mol) in chloroform (50 ml). The solution was stirred at 0° C. for 1 hour and at room temperature for 2 hours. Dichloromethane (200 ml) and water (400 ml) ware added and the organic phase was washed further with water (400 ml), brine (200 ml) and dried (MgSO$_4$). The solvent was removed and the residue was purified by distillation at reduced pressure to give the title compound. $^1$H NMR (250 MHz, CDCl$_3$) δ 7.38 (1H, d, J=2.1 Hz), 7.13 (1H, dd, J=9.1, 2.1 Hz), 7.03 (1H, d, J=9.1 Hz), and 5.53 (1H, s).

PREPARATION 9

2-Benzyloxy-5-(trifluoromethoxy)bromobenzene

2-Bromo-4-(trifluoromethoxy)phenol (Preparation 8; 5 g, 20 mmol) was dissolved in N,N-dimethylformamide (60 ml), and potassium carbonate (5.4 g, 40 mmol) was added, followed by benzyl bromide (3.5 ml, 30 mmol), and the reaction was stirred at ambient temperature for 15 hours. The reaction was diluted with water (150 ml) and extracted into ethyl acetate (3×60 ml). The combined organic fractions were washed with water (100 ml), brine (100 ml), dried (MgSO$_4$) and evaporated in vacuo. Purification on silica, eluting with 2% and 5% ethyl acetate in hexane gave the title compound as a clear oil (6.7 g, 96%). $^1$H NMR (250 MHz, CDCl$_3$) δ 5.47 (2H, s), 7.23 (1H, d, J=9 Hz), 7.43 (1H, dd J=8.2, 2.9 Hz), and 7.75 (6H, m).

PREPARATION 10
Z-(2S,3R)-1-tert-Butoxycarbonyl-3-(3-hydroxyprop-1-en-1-yl)-2-phenylpiperidin-3-ol Palladium on calcium carbonate, poisoned with lead (Lindlar catalyst, 2 g) was added to a solution of (2S,3R)-1-tert-butoxycarbonyl-3-(3-hydroxypropyn-1yl)-2-phenylpiperidin-3-ol (Preparation 7; 32 g, 96.6 mmol) in ethyl acetate (300 ml) and the mixture was stirred under hydrogen (1 atmosphere) for 4 hours. The mixture was filtered and the solvent was evaporated under reduced pressure to give the title compound as an oil (32 g, 100%). $^1$H NMR (360 MHz, CDCl$_3$) δ 7.42 (2H, d, J=7.6 Hz), 7.35–7.25 (3H, m), 5.83 (1H, d, J12.3 Hz), 5.68 (1H, dt, J=12.3, 6.0 Hz), 5.06 (1H, s), 4.27 (1H, m), 4.12 (2H, m), 3.32 (1H, m), 3.13 (1H, s), 2.28 (1H, t, J=5.9 Hz), 2.02 (1H, m), 1.92–1.78 (3H, m), and 1.32 (9H, s). m/z (ES$^+$) 334 (M+1).

PREPARATION 11
(5R,6S)-6-Phenyl-1-oxa-7-(tert-butoxycarbonyl)aza-spiro[4.5]dec-3-ene Diethylazodicarboxylate (18.2 ml, 115 mmol) in THF (100 ml) was added dropwise to a solution of Z-(2S,3R)-1-tert-butoxycarbonyl-3-(3-hydroxyprop-1-en-1-yl)-2-phenylpiperidin-3-ol (Preparation 10; 32 g, 96 mmol) and triphenylphosphine (30.2 g, 115 mmol) in THF (700 ml). The mixture was stirred at 0° C. for 30 minutes then at room temperature for 1.5 hours. The solvent was evaporated under reduced pressure and the residue was purified by flash column chromatography on silica gel, eluting with hexane/ethyl acetate (95:5 increasing to 80:20) to give the title compound as a colorless solid (23.4 g, 77%). $^1$H NMR (CDCl$_3$) δ 7.45 (2H, d, J=7.4 Hz), 7.27 (2H, t, J=7.4 Hz), 7.20 (1H, t, J=7.4 Hz), 6.03 (1H, dt, J=6.1, 2.0 Hz), 5.68 (1H, dt, J=6.1, 2.0 Hz), 5.06 (1H, s), 4.61 (1H, dt, J=13.1, 2.0 Hz), 4.32 (1H, dt, J=13.1, 2.0 Hz), 4.08 (1H, m), 3.05 (1H, m), 2.05 (1H, m), 1.75 (3H, m), and 1.37 (9H, s). m/z (ES$^+$) 316 (M+1).

PREPARATION 12
2-Benzyloxy-5-(trifluoromethoxy)benzene

Benzyl bromide (66.17 ml, 95.35 g, 0.56 mol) was added to a mixture of 4-(trifluoromethoxy)phenol (90.26 g, 0.51 mol) and potassium carbonate (140.97 g, 1.2 mol) in dimethylformamide (160 ml) and the mixture was stirred at room temperature for 72 hours. The mixture was poured into water (1.5 l) and extracted with ethyl acetate (3×50 ml). The combined organic fractions were washed with aqueous sodium carbonate (saturated, 500 ml), dried (MgSO$_4$) and the solvent was evaporated under reduced pressure to give the title compound as a colorless solid (133.5 g, 99%). $^1$H NMR (360 MHz, CDCl$_3$) δ 7.39 (5H, m), 7.14 (2H, d, J=9.0 Hz), 6.95 (2H, d, J=9.0 Hz), and 5.05 (2H, s).

PREPARATION 13
2-Benzyloxy-5-(trifluoromethoxy)iodobenzene

Iodine (71.96 g, 0.28 mol) in chloroform was added dropwise to a mixture of 2-benzyloxy-5-(trifluoromethoxy)benzene (Preparation 12, 73.06 g, 0.27 mol) and silver trifluoroacetate (71.57 g, 0.32 mol) in dichloromethane and the mixture was stirred at room temperature for 18 hours. The mixture was filtered through celite, washed with aqueous sodium thiosulfate (5%, 2×2 l), dried (MgSO$_4$) and the solvent was evaporated under reduced pressure. The residue was purified by flash column chromatography on silica gel, eluting with hexane/ethyl acetate, to give the title compound as a colorless oil (108.03 g), containing 11% unreacted 2-benzyloxy-5-(trifluoromethoxy)iodobenzene. $^1$H NMR (360 MHz, CDCl$_3$) δ 7.67 (1H, d, J=2.8 Hz), 7.40 (5H, m), 7.16 (1H, dd, J=8.9, 2.8 Hz), 6.82 (1H, d, J=8.9 Hz), and 5.14 (2H, s).

PREPARATION 14
(5R,6S)-3-(2-Benzyloxy-5-(trifluoromethoxy)phenyl)-6-phenyl-1-oxa-7-(tert-butoxycarbonyl)aza-spiro[4.5]dec-3-ene (5R,6S)-3-Trimethylstannyl-6-phenyl-1-oxa-7-(tert-butoxycarbonyl)aza-spiro[4.5]dec-3-ene (Preparation 6; 6.43 mmol), lithium chloride (0.163 g), benzyloxy-5-(trifluoromethoxy)phenol (Preparation 9; 7.7 mmol) in toluene (25 ml) was degassed before addition of triphenyiphosphine palladium (0) (0.37 g). The solution was degassed thoroughly before heating to 110° C. for 14 hours. The solution was partitioned between water and ethyl acetate and the dried organic phase was purified by chromatography on a column containing silica gel (eluting with hexane containing increasing proportions of ethyl acetate between 0% to 4%) to give the title compound. $^1$H NMR (360 MHz, CDCl$_3$) δ 1.33 (9H, s), 1.65 (1H, m), 1.76 (2H, m), 2.08 (1H, m), 3.11 (1H, m), 4.08 (1H, m), 4.60 (1H, dd, J=12.2 Hz, J=2 Hz), 4.92 (1H, dd, J=12.1 Hz, J=1.8 Hz), 5.08 (1H, s), 5.1 (2H, q, J=11.5 Hz), 6.65 (1H, s), 6.94 (2H, d, J=8.9 Hz), 7.08 (1H, d, J=9 Hz), 7.18 (2H, t, J=8.1 Hz), 7.25 (3H, m), 7.38 (5H, m).

PREPARATION 15
(3S,5R,6S)-3-(2-Hydroxy-5-trifluoromethoxy)phenyl)-6-phenyl-1-oxa-7-(tert-butoxycarbonyl)aza-spiro[4.5]decane (5R,6S)-3-(2-Benzyloxy-5-(trifluoromethoxy)phenyl)-6-phenyl-1-oxa-7-(tert-butoxycarbonyl)aza-spiro[4.5]dec-3-ene (Preparation 14) (3.88 g) was dissolved in ethyl acetate (15 ml) and methanol (15 ml). Palladium hydroxide on carbon (1.00 g) was added and the suspension was shaken under a hydrogen atmosphere (50 psi) for 72 hours. The mixture was filtered and the solvent was evaporated under reduced pressure. The residue was purified by medium pressure chromatography on silica gel, eluting with hexane/ethyl acetate (75:25) to give (3R,5R,6S)-3-(2-hydroxy-5-(trifluoromethoxy)phenyl)-6-phenyl-1-oxa-7-(tert-butoxycarbonyl)aza-spiro[4.5]decane (191 mg), $^1$H NMR (250 MHz, CDCl$_3$) δ 7.70 (2H, d, J=7.3 Hz), 7.33 (2H, t, J=7.3 Hz), 7.26 (1H, d, J=7.3 Hz), 7.05 (1H, br s), 6.96 (2H, m), 6.82 (1H, d, J=9.4 Hz), 5.43 (1H, s), 4.27 (1H, m), 4.01 (1H, m), 3.95 (1H, m), 3.73 (1H, m), 2.73 (2H, m), 2.33 (1H, m), 1.87–1.58 (4H, m); and 1.50 (9H, s).and (3S,5R,6S)-3-(2-hydroxy-5-(trifluoromethoxy)phenyl)-6-phenyl-1-oxa-7-(tert-butoxycarbonyl)aza-spiro[4.5]decane (2.3 g), $^1$H NMR (360 MHz, CDCl$_3$) δ 1.38 (9H, s), 1.73 (2H, m), 1.81 (1H, m), 2.18 (2H, m), 2.50 (1H, m), 2.81 (1H, m), 3.62 (1H, t, J=7.2 Hz), 3.92 (1H, m), 3.98 (1H, d, J=13.2 Hz), 4.23 (1H, m), 5.33 (1H, s), 6.75 (1H, d, J=8.5 Hz), 6.94 (2H, m), 7.25 (1H, m), 7.31 (2H, m), and 7.55 (2H, d, J=7.8 Hz).

PREPARATION 16
(3R,5R,6S)-3-(2-Benzyloxy-5-(trifluoromethoxy)phenyl)-6-phenyl-1-oxa-7-(tert-butoxycarbonyl)aza-spiro[4.5]decane A mixture of 2-benzyloxy-5-(trifluoromethoxy)iodobenzene (Preparation 13, 21.8 g, 55.2 mmol), (5R,6S)-6-phenyl-1-oxa-7-(tert-butoxycarbonyl)aza-spiro[4.5]dec-3-ene (Preparation 11, 7.0 g, 22.1 mmol), tetra-n-butylammonium chloride (6.18 g, 22.2 mmol), lithium chloride (9.35 g, 0.22 mol) and potassium formate (5.64 g, 67.0 mmol) in dimethylformamide (100 ml) was degassed with a firestone valve (5 x). Palladium acetate (491 mg, 2.2 mmol) was added and the mixture was degassed with a firestone valve (5 x). The mixture was stirred at 60° C. for 15 hours, then further 2-benzyloxy-5-(trifluoromethoxy) iodobenzene (Preparation 13, 4.32 g, 11.0 mmol), potassium formate (2.78 g, 33.5 mmol) and palladium acetate (260 mg, 1.1 mmol) were added. The mixture was stirred at 60° C. for 22 hours, cooled and filtered. The solvent was evaporated under reduced pressure, water (600 ml) was added and the mixture was extracted with ethyl acetate (2×300 ml). The combined organic fractions were washed with brine (300 ml), dried (MgSO$_4$) and the solvent was evaporated under reduced pressure. The residue was purified by flash column chromatography on silica gel, eluting with hexane/ dichloromethane (75:25 increasing to 0:100) then dichloromethane/ethyl acetate (95:5), to give the title compound (9.42 g, 73%). $^1$H NMR (360 MHz, CDCl$_3$) δ 7.56 (2H, d, J=7.7 Hz), 7.40–7.20 (8H, m), 7.14 (1H, d, J=2.0 Hz), 7.00 (1H, dd, J=8.9, 2.0 Hz), 6.88 (1H, d, J=8.9 Hz), 5.30 (1H, s), 5.08 (2H, s), 4.27 (1H, m), 3.97 (1H, m), 3.87 (2H, m), 2.78 (1H, m), 2.56 (1H, m), 2.15 (1H, m), 1.96 (1H, m), 1.67 (3H, m), and 1.42 (9H, s).

PREPARATION 17
(3R,5R,6S)-3-(2-Hydroxy-5-(trifluoromethoxy)phenyl)-6-phenyl-1-oxa-7-(tert-butoxycarbonyl)aza-spiro[4.5]decane Palladium on carbon (10%, 0.59 g) was added to a solution of (3R,5R,6S)-3-(2-benzyloxy-5-(trifluoromethoxy)phenyl)-6-phenyl-1-oxa-7-(tert-butoxycarbonyl)aza-spiro[4.5]decane (Preparation 16, 6.10 g, 10.5 mmol) in methanol-water (99:1, 200 ml) and the mixture was stirred under hydrogen (50 psi.) for 72 hours. The mixture was filtered, washing with ethanol, and the solvent was evaporated under reduced pressure. The residue was purified by flash column chromatography on silica gel, eluting with dichloromethane/ethyl acetate (99:1 increasing to 90:10) to give the title compound. $^1$H NMR (360 MHz, CDCl$_3$) δ 7.70 (2H, d, J=7.3 Hz), 7.33 (2H, t, J=7.3 Hz), 7.26 (1H, d, J=7.3 Hz), 7.05 (1H, br s), 6.96 (2H, m), 6.82 (1H, d, J=9.4 Hz), 5.43 (1H, s), 4.27 (1H, m), 4.01 (1H, m), 3.95 (1H, m), 3.73 (1H, m), 2.73 (2H, m), 2.33 (1H, m), 1.87–1.58 (4H, m), and 1.50 (9H, s).

PREPARATION 18
(3S,5R,6S)-3-[2-(1-Phenylthiocycloprop-1-yl)oxy-5-(trifluoromethoxy)phenyl]-6-phenyl-1-oxa-7-(tert-butoxycarbonyl)aza-spiro[4.5]decane (3S,5R,6S)-3-(2-Hydroxy-5-(trifluoromethoxy)phenyl)-6-phenyl-1-oxa-7-(tert-butoxycarbonyl)aza-spiro[4.5] decane (Preparation 15) (290 mg, 0.59 mmol) was dissolved in toluene (5 ml) and silver carbonate (179 mg, 0.65 mmol) was added in one portion. (1-Iodocycloprop-1-yl) phenylsulfide (Cohen T. and Matz J. R., *J. Am. Chem. Soc.* 1980, 102, 6902) (180 mg, 0.65 mmol) was then added over one minute at room temperature. The mixture was stirred at 55° C. for 4 hours, then further portions of silver carbonate (179 mg, 0.65 mmol) and (1-iodocycloprop-1-yl) phenylsulfide (180 mg, 0.65 mmol) were added. The mixture was stirred at 55° C. for a further 3 hours, cooled, filtered and the solvent was evaporated under reduced pressure. The residue was purified by column chromatography on silica gel, eluting with hexane/ethyl acetate (90:10 increasing to 80:20) to give the title compound as a colourless oil (120 mg, 32%). $^1$H NMR (250 MHz, CDCl$_3$) δ 7.55–7.44 (4H, m), 7.36–7.23 (7H, m), 7.13–7.02 (2H, m), 5.16 (1H, br s), 4.09 (1H, t, J=6 Hz), 4.03–3.92 (1H, m), 3.67–3.49 (2H, m), 2.94–2.79 (1H, m), 2.26 (1H, dd, J=7.9, 12.9 Hz), 2.15–2.01 (2H, m), 1.76–1.59 (3H, m), 1.53–1.45 (4H, m), and 1.36 (9H, s). m/z (ES$^+$) 642 (M+1).

PREPARATION 19
(3R,5R,6S)-3-[2-(1-Phenylthiocycloprop-1-yl)oxy-5-(trifluoromethoxy)phenyl]-6-phenyl-1-oxa-7-(tert-butoxycarbonyl)aza-spiro[4.5]decane Prepared from (3R,5R,6S)-3-(2-hydroxy-5-(trifluoromethoxy)phenyl)-6-phenyl-1-oxa-7-(tert-butoxycarbonyl)aza-spiro[4.5]decane (Preparation 17) according to the method of Preparation 18. $^1$H NMR (360 MHz, CDCl$_3$) δ 7.57 (2H, app. d, J=7.6 Hz), 7.45 (2H, app. d, J=7.7 Hz), 7.36–7.19 (7H, m), 7.16–7.06 (2H, m), 5.28 (1H, br s), 4.13 (1H, app. t, J=7.8 Hz), 3.96 (1H, br. d, J=13 Hz), 3.80–3.60 (2H, m), 2.79 (1H, br. t, J=13 Hz), 2.50 (1H, dd, J=13, 7.9 Hz), 2.17 (1H, dt, J=13, 4.6 Hz), 1.80 (1H, dd, J=12, 9.8 Hz), 1.75–1.38 (7H, m), and 1.44 (9H, s). m/z (ES$^+$) 642 (M+1).

PREPARATION 20
(3S,5R,6S)-3-[2-Cyclopropoxy-5-(trifluoromethoxy) phenyl]-6-phenyl-1-oxa-7-(tert-butoxycarbonyl)aza-spiro [4.5]decane Naphthalene (120 mg, 0.936 mmol) was dissolved in THF (1.5 ml) under nitrogen and freshly cut lithium metal (7.0 mg, 0.94 mmol) was added. The mixture was then sonicated at room temperature for 20 minutes to produce a dark green solution of lithium naphthalenide. This solution was cooled to −78° C., then (3S,5R,6S)-3-[2-(1-phenylthiocycloprop-1-yl)oxy-5-(trifluoromethoxy)phenyl]-6-phenyl-1-oxa-7-(tert-butoxycarbonyl)aza-spiro[4.5]decane (Preparation 18) (120 mg, 0.187 mmol) in THF (0.5 ml) was added over 1 minute. The reaction mixture was stirred for 30 minutes, then water (5 ml) and ether (10 ml) were added. The layers were separated and the aqueous layer was extracted with ether (10 ml). The combined organic fractions were dried (MgSO$_4$) and the solvent was evaporated under reduced pressure. The residue was purified by column chromatography on silica gel, eluting with hexane/ethyl acetate (90:10 increasing to 80:20) to give the title compound as a colourless oil (58.6 mg, 59%). $^1$H NMR (250 MHz, CDCl$_3$) δ 7.58–7.52 (2H, m), 7.36–7.17 (4H, m), 7.10–7.01 (2H, m), 5.18 (1H, br s), 4.20 (1H, t, J=6.7 Hz), 4.05–3.95 (1H, m), 3.76–3.55 (3H, m), 2.92–2.79 (1H, m), 2.37 (1H, dd, J=12.9, 7.8 Hz), 2.18–2.06 (2H, m), 1.80–1.67 (3H, m), 1.38 (9H, s), and 0.86–0.73 (4H, m). m/z (ES$^+$) 534 (M+1).

PREPARATION 21
(3R,5R,6S)-3-[2-Cyclopropoxy-5-(trifluoromethoxy) phenyl]-6-phenyl-1-oxa-7-(tert-butoxycarbonyl)aza-spiro [4.5]decane Naphthalene (120 mg, 0.936 mmol) was dissolved in THF (1.5 ml) under nitrogen and freshly cut lithium metal (7.0 mg, 0.94 mmol) was added. The mixture was then sonicated at room temperature for 20 minutes to produce a dark green solution of lithium naphthalenide. A solution of (3R,5R,6S)-3-[2-(1-phenylthiocycloprop-1-yl)oxy-5-(trifluoromethoxy) phenyl]-6-phenyl-1-oxa-7-(tert-butoxycarbonyl)aza-spiro [4.5]decane (Preparation 19, 135 mg, 0.21 mmol) in THF (2 ml) under nitrogen was cooled to −78° C. and the solution of lithium naphthalenide in THF was added dropwise until the intense green colour persisted. The reaction was then stirred for one minute, water (5 ml) was added and the mixture was warmed to room temperature. Ether (10 ml) was added and the layers were separated. The aqueous phase was extracted with a further portion of ether (10 ml) and the combined organic phases were dried (MgSO$_4$) and the solvent was evaporated under reduced pressure. The residue was purified by column chromatography on silica gel, eluting with hexane/ethyl acetate (50:50) to give the title compound as a colourless oil (87 mg, 78%). $^1$H NMR (360 MHz, CDCl$_3$) δ 7.59 (2H, app. d, J=7.6 Hz), 7.32 (2H, app. t, J=7.6 Hz), 7.27–7.18 (2H, m), 7.11–7.03 (2H, m), 5.32 (1H, br s), 4.29–4.21 (1H, m), 3.97 (1H, br. d, J=13 Hz), 3.83–3.68 (3H, m), 2.76 (1H, dt, J=13, 4.1 Hz), 2.55 (1H, dd, J=13, 7.2 Hz), 2.22 (1H, dt, J=12, 5.2 Hz), 1.85 (1H, dd, J=13, 9.9 Hz), 1.80–1.63 (3H, m), 1.46 (9H, s), and 0.82–0.76 (4H, m). m/z (ES$^+$) 534 (M+1).

COMPOUND A
(3S,5R,6S)-3-[2-Cyclopropoxy-5-(trifluoromethoxy) phenyl]-6-phenyl-1-oxa-7-aza-spiro[4.5]decane Hydrochloride Trifluoroacetic acid (2.5 ml) was added dropwise to a stirred, cooled 0° C.) solution of (3S,5R,6S)-3-[2-cyclopropoxy-5-(trifluoromethoxy)phenyl]-6-phenyl-1-oxa-7-(tert-butoxycarbonyl)aza-spiro[4.5]decane (Preparation 20; 492 mg, 0.92 mmol) in dichloromethane (25 ml) and the mixture was stirred at room temperature for 3 hours. The mixture was poured into water (50 ml), the pH was adjusted to 10.0 with aqueous sodium hydroxide (4M) and the mixture was extracted with dichloromethane (3×50 ml). The combined organic fractions were dried (MgSO$_4$) and the solvent was evaporated under reduced pressure. The residue was purified by flash column chromatography on silica gel, eluting with dichloromethane/methanol/ammonia (aq.) (96:4:0.4 increasing to 94:6:0.6). The residue was dissolved in ethanol (20 ml), cooled in ice and ethereal hydrogen chloride (1M, 1.8 ml, 1.8 mmol) was added dropwise. The mixture was stirred at 0° C. for 5 minutes, then the solvent was evaporated under reduced pressure. The residue was crystallized from ether (20 ml)/ethanol (0.5 ml) and the solid was collected and dried in vacuo to give the title compound as a colorless solid (354 mg, 89%). m.p. 214–216° C., $^1$H NMR (500 MHz, CD$_3$OD) δ 7.59 (2H, m), 7.52 (3H, m), 7.26 (1H, d, J=8.9 Hz), 7.03 (1H, dd, J=8.9, 2.2 Hz), 6.20 (1H, d, J=2.2 Hz), 4.85 (2H, br s), 4.43 (1H, s), 4.19 (1H, t, J=8.0 Hz), 3.87 (1H, quin, J=8.0 Hz), 3.76 (1H, m), 3.44 (1H, m), 3.25 (2H, m) 2.29–1.78 (6H, m), 0.80 (2H, m), and 0.66 (2H, m). m/z (ES$^+$) 434 (M+1). Found: C, 61.41; H, 5.51; N, 3.08. C$_{24}$H$_{26}$F$_3$NO$_3$.HCl requires: C, 61.34; H, 5.79; N, 2.98%.

COMPOUND B
(3R,5R,6S)-3-[2-Cyclopropoxy-5-(trifluoromethoxy) phenyl]-6-phenyl-1-oxa-7-aza-spiro[4.5]decane Prepared from the compound of Preparation 21 according to the method used for Compound A. $^1$H NMR (360 MHz, CDCl$_3$) δ 7.50–7.42 (2H, m), 7.36–7.26 (3H, m), 7.03 (1H, d, J=8.9 Hz), 6.95 (1H, br. d, J=8.9 Hz), 6.81 (1H, br s), 3.92 (1H, t, J=7.4 Hz), 3.62–3.53 (2H, m), 3.50 (1H, s), 3.20 (1H, dd, J=12, 4.2 Hz), 2.77 (1H, dt, J=12, 2.8 Hz), 2.30–1.93 (4H, m), 1.87 (1H, br s), 1.71–1.49 (3H, m), 0.76–0.65 (2H, m), and 0.65–0.54 (2H, m). m/z (ES$^+$) 434 (M+1).

A further compound and diastereomers thereof of use in the present invention may be prepared according to the following methods:

DESCRIPTION 1
2-(1-Phenylthiocycloprop-1-yl)oxy-5-(trifluoromethoxy) benzaldehyde Silver carbonate (1.2 g, 4.34 mmol) was added to a solution of 2-hydroxy-5-(trifluoromethoxy)benzaldehyde (0.5 g, 2.43 mmol) and (1-iodocycloprop-1-yl)phenylsulfide (Cohen T. and Matz J. R., *J. Am. Chem. Soc.* 1980, 102, 6902) (1.2 g, 4.34 mmol) in toluene (30 mL) and the mixture was stirred at 40° C. overnight. The mixture was cooled, diluted with ethyl acetate and filtered, washing well with ethyl acetate. The mixture was washed with aqueous sodium hydroxide, dried (MgSO$_4$) and the solvent was evaporated under reduced pressure. The residue was purified by flash column chromatography on silica gel, eluting with hexane/Et$_2$O (95:5), to give the title compound as a yellow oil (191 mg, 27%). $^1$H NMR (360 MHz, CDCl$_3$) δ 1.51–1.56 (2H, m), 1.44–1.48 (2H, m), 7.25–7.35 (7H, m), 7.69 (1H, d, J 2.0 Hz), and 10.26 (1H, s).

DESCRIPTION 2
2-Cyclopropoxy-5-(trifluoromethoxy)benzaldehyde

Freshly cut lithium metal (97 mg, 13.9 mmol) was added to a solution of naphthalene (1.77 g, 13.9 mmol) in THF (20 mL) and the mixture was sonicated at room temperature for 30 min. to produce a dark green solution of lithium naphthalenide. A solution of 2-(1-phenylthiocycloprop-1-yl)oxy-5-(trifluoromethoxy)benzaldehyde (Description 1, 96 mg, 0.27 mmol) in THF (2 mL) was cooled to −78° C. and the solution of lithium naphthalenide in THF (2 mL) was added dropwise until the intense green colour persisted. The reaction was then stirred for 5 min., water (6 mL) was added and the mixture was warmed to room temperature. The mixture was extracted with ethyl acetate, the combined organic fractions were dried (MgSO$_4$) and the solvent was evaporated under reduced pressure. The residue was purified by flash column chromatography on silica gel, eluting with hexane/Et$_2$O (80:20), to give to give the title compound as a colourless oil (4 mg, 6%). $^1$H NMR (360 MHz, CDCl$_3$) δ 0.86 (4H, m), 3.82–3.9 (1H, m), 7.42 (2H, m), 7.62 (1H, d, J 2.5 Hz), and 10.36 (1H, s).

DESCRIPTION 3
2-Nitro-4-(trifluoromethoxy)phenol

Iron(111)nitrate nonahydrate (1.97 g, 4.87 mmol) was added to a solution of 4-(trifluoromethoxy)phenol (2 g, 11.24 mmol) in ethanol (20 mL) and the mixture was heated under reflux overnight. The mixture was allowed to cool to room temperature, acidified to pH 1 with aqueous hydrochloric acid (1M) and extracted with ethyl acetate. The combined organic fractions were dried (MgSO$_4$), and the solvent was evaporated under reduced pressure. The residue was purified by short column chromatography on silica gel, eluting with hexane/EtOAc (70:30), to give the title compound as a yellow oil (2.25 g, 89%). $^1$H NMR (360 MHz, CDCl$_3$) δ 10.53 (1H, s), 8.01 (1H, d, J 3.0 Hz), 7.49 (1H, dd, J 9.1, 3.0 Hz), and 7.23 (1H, d, J 9.1 Hz).

DESCRIPTION 4
2-(1-Phenylthiocycloprop-1-yl)oxy-5-(trifluoromethoxy) nitrobenzene Prepared from the compound of Description 3 according to the method of Description 1. $^1$H NMR (360 MHz, CDCl$_3$) δ 7.73 (1H, d, J 2.7 Hz), 7.58 (1H, d, J 9.2 Hz), 7.50–7.24 (6H, m), 1.57–1.53 (2H, m), and 1.44–1.40 (2H, m).

DESCRIPTION 5
2-Cyclopropoxy-5-(trifluoromethoxy)benzeneamine

Prepared from the compound of Description 4 according to the method of Description 2. $^1$H NMR (360 MHz, CDCl$_3$) δ 7.06 (1H, dd, J 2.8, 6.7 Hz), 6.56 (2H, m), 3.83 (2H, br s), 3.74 (1H, m), and 0.79 (4H, m). m/z (ES$^+$) 234 (M+1).

DESCRIPTION 6
2-(1-Phenylthiocycloprop-1-yl)oxy-5-(trifluoromethoxy) benzeneamine Iron powder (13.5 g, 241 mmol) was added to a suspension of 2-(1-phenylthiocycloprop-1-yl)oxy-5-(trifluoromethoxy)nitrobenzene (Description 4, 11.27 g, 30.1 mmol) in water (300 mL) and acetic acid (75 mL) and the mixture was stirred at 80° C. overnight. The mixture was cooled and filtered through celite, washing with ether. The filtrate was extracted with ether, the combined organic fractions were washed with aqueous sodium hydroxide (1M), dried (MgSO$_4$), and the solvent was evaporated under reduced pressure. The residue was purified by flash column chromatography on silica gel, eluting with hexane/Et$_2$O (90:10 increasing to 80:20), to give the title compound as a yellow solid (8 g, 78%). $^1$H NMR (360 MHz, CDCl$_3$) δ 7.48 (2H, m), 7.34–7.23 (3H, m), 7.15 (1H, d, J 8.74 Hz), 6.60–6.56 (2H, m), 3.78 (2H, br s), 1.49–1.46 (2H, m), and 1.39–1.35 (2H, m).

DESCRIPTION 7

2-Cyclopropoxy-5-(trifluoromethoxy)benzeneamine

Prepared from the compound of Description 6 according to the method of Description 2. $^1$H NMR (360 MHz, CDCl$_3$) δ 7.06 (1H, dd, J 2.8, 6.7 Hz), 6.56 (2H, m), 3.83 (2H, br s), 3.74 (1H, m), and 0.79 (4H, m). m/z (ES$^+$) 234 (M+1).

DESCRIPTION 8

2-Cyclopropoxy-5-(trifluoromethoxy)iodobenzene

An ice-cooled solution of sodium nitrite (3.55 g, 51 mmol) in water (10 mL) was added dropwise to a stirred, cooled (0° C.) solution of 2-cyclopropoxy-5-(trifluoromethoxy)benzeneamine (Description 7, 4.8 g, 20.6 mmol) in aqueous hydrochloric acid (5M, 300 mL), maintaining the internal temperature at 0° C. The mixture was stirred at 0° C. for 30 min., then potassium iodide (8.55 g, 51.5 mmol) in water (10 mL) was added dropwise, maintaining the internal temperature at 0° C. The mixture was stirred at 0° C. for 30 min., then allowed to warm up to room temperature and stirred until nitrogen evolution ceased. The mixture was extracted with ether, the organic fraction was washed with aqueous sodium thiosulfate (10%), dried (MgSO$_4$), and the solvent was evaporated under reduced pressure. The residue was purified by flash column chromatography on silica gel, eluting with hexane/Et$_2$O (98:2 increasing to 95:5), to give the title compound as a colourless oil (6.23 g, 88%). $^1$H NMR (360 MHz, CDCl$_3$) δ 7.62 (1H, d, J 2.4 Hz), 7.20 (1H, dd, J 9.1, 2.4 Hz), 7.15 (1H, d, J 9.1 Hz), 3.80 (1H, m), and 0.83 (4H, m).

DESCRIPTION 9

2-Cyclopropoxy-5-(trifluoromethoxy)benzaldehyde

A solution of 2-cyclopropoxy-5-(trifluoromethoxy) iodobenzene (Description 8, 0.344 g, 1 mmol) in toluene (2.5 mL) was degassed with bubbling nitrogen for 10 min. Tetrakis(triphenylphosphine)palladium (0) (15 mg) was added, the mixture was degassed with bubbling nitrogen for a further 5 min., then carbon monoxide was bubbled through the mixture for 10 min. The mixture was warmed to 50° C. and a solution of tributyl tin hydride (0.3 mL, 1.1 mmol) in toluene (5 mL) was added at a rate of 2 mL/h. via a syringe pump, maintaining carbon monoxide bubbling throughout. The mixture was cooled, diluted with ether (20 mL) and aqueous potassium fluoride solution (50%) was added. The mixture was stirred at room temperature overnight, filtered and the layers were separated. The organic layer was dried (MgSO$_4$), and the solvent was evaporated under reduced pressure. The residue was purified by flash column chromatography on silica gel, eluting with hexane/Et$_2$O (80:20), to give the title compound as a colourless oil. 1H NMR (360 MHz, CDCl$_3$) δ 0.86 (4H, m), 3.82–3.9 (1H, m), 7.42 (2H, m), 7.62 (1H, d, J 2.5 Hz), and 10.36 (1H, s).

DESCRIPTION 10

(±)-(2RS)-1-tert-Butoxycarbonyl-2-phenylpiperidin-3-one

Dimethyl sulfoxide (32.0 mL, 35.3 g, 0.45 mol) in dichloromethane (100 mL) was added dropwise to a cooled (−70° C.) solution of oxalyl chloride (18.7 mL, 27.5 g, 0.22 mol) in dichloromethane (1000 mL). The mixture was stirred at −70° C. for 15 min., then (2S,3S)-1-tert-butoxycarbonyl-3-hydroxy-2-phenylpiperidine (prepared by the method described in European Patent Specification number 0 528 495-A; 50 g, 0.18 mol) in dichloromethane (150 mL) was added dropwise. The mixture was stirred at −70° C. for 1 h., then triethylamine (125.8 mL, 91.3 g, 0.9 mol) was added slowly. The mixture was stirred at room temperature for 1 h., water (250 mL) and aqueous sodium hydrogen carbonate (saturated, 250 mL) were added and the mixture was stirred at room temperature overnight. The layers were separated and the aqueous layer was extracted with dichloromethane (2×300 mL). The combined organic fractions were washed with brine, dried (MgSO$_4$) and the solvent was evaporated under reduced pressure. The residue was purified by flash column chromatography on silica gel, eluting with hexane/EtOAc (90:10), to give the title compound as a yellow oil (45.0 g, 91%). $^1$H NMR (250 MHz, CDCl$_3$) δ 7.5–7.3 (5H, m), 5.8 (1H, br s), 4.2 (1H, br s), 3.4 (1H, m), 2.6 (2H, m), 2.0 (2H, m), and 1.54 (9H, s).

DESCRIPTION 11

(±)-(2R3R,2S3S)-1-(tert-Butoxycarbonyl)-2-phenylpiperidin-3-amine

A solution of hydroxylamine hydrochloride (17 g, 0.24 mol) and sodium acetate (55.67 g, 0.41 mol) in water (150 mL) was added to a solution of (±)-(2RS)-1-tert-butoxycarbonyl-2-phenylpiperidin-3-one (Description 10, 45 g, 0.16 mol) in ethanol (300 mL) and the mixture was stirred at room temperature for 1 h. The solvent was evaporated under reduced pressure, water was added and the mixture was extracted with ethyl acetate. The organic fraction was washed with brine, dried (MgSO$_4$) and the solvent was evaporated under reduced pressure. The residue was dissolved in ethanol (400 mL) and Raney nickel (50 g) was added. The mixture was shaken under hydrogen (40 psi) overnight, filtered and the solvent was evaporated under reduced pressure. The residue was purified by flash column chromatography on silica gel, eluting with CH$_2$Cl$_2$/MeOH (100:0 increasing to 85:15), to give the title compound as a colorless oil (10.9 g, 24%). $^1$H NMR (360 MHz, CDCl$_3$) δ 7.43 (2H, d, J 7.0 Hz), 7.30 (3H, m), 5.19 (1H, d, J 6.2 Hz), 4.00 (1H, m), 3.17 (2H, m), 1.90–1.64 (4H, m), 1.36 (9H, s), and 1.26 (2H, br s).

COMPOUND C (±)-(2R3R,2S3S)-N-{[2-Cyclopropoxy-5-(trifluoromethoxy)phenyl]methyl}-2-phenylpiperidin-3-amine Dihydrochloride 2-Cyclopropoxy-5-(trifluoromethoxy)benzaldehyde (Description 9, 55 mg, 0.21 mmol) was added to (±)-(2R3R, 2S3S)-1-(tert-butoxycarbonyl)-2-phenylpiperidin-3-amine (Description 11, 58 mg, 0.21 mmol), citric acid (89 mg, 0.42 mmol) and 3 Å molecular sieves in dry methanol (5 mL) and the mixture was stirred at room temperature for 1.5 h. Sodium borohydride (30 mg) was added and the mixture was stirred at room temperature for 2 h. Ethyl acetate was added and the mixture was washed with aqueous hydrochloric acid (0.1M, 2×25 mL) and brine (25 mL), dried (MgSO$_4$) and the solvent was evaporated under reduced pressure. The residue was dissolved in dichloromethane (3 mL), cooled to 0° C. and trifluoroacetic acid (2 mL) was added slowly. The mixture was stirred at room temperature for 1 h., the solvent was evaporated under reduced pressure and ethyl acetate was added. The mixture was washed with aqueous sodium hydrogen carbonate (saturated, 2×25 mL) and brine (25 mL), dried (MgSO$_4$) and the solvent was evaporated under reduced pressure. The residue was purified by flash column chromatography on silica gel, eluting with CH$_2$Cl$_2$/MeOH/NH$_3$(Aq.) (96:4:0.4). The residue was dissolved in ethanol (2 mL), cooled in ice and ethereal hydrogen chloride (1M, 0.24 mL, 0.24 mmol) was added. The solvent was evaporated under reduced pressure and the residue was recrystallised from ethanol to give the title compound as a colorless solid (20 mg, 20%). m.p. 169–171° C. $^1$H NMR (400 MHz, CD$_3$OD) δ 0.64 (1H, m), 0.80 (3H, m), 1.99 (1H, m), 2.24 (1H, m), 2.46 (2H, m), 3.30 (1H, m), 3.64 (1H, m), 3.75 (2H, m), 3.96 (1H, br s), 4.08 (1H, m), 4.95 (1H, s), 7.23 (1H, s), 7.31 (1H, d, J 9.0 Hz), 7.37 (1H, d, J 9.0 Hz), 7.54 (3H, m), and 7.67 (2H, m). m/z (ES$^+$) 407 (M+1).

Particularly preferred NK-1 receptor antagonists of use in the present invention are compounds which are potent NK-1 receptor antagonists, i.e. compounds with an NK-1 receptor affinity (IC$_{50}$) of less than 10 nM, favourably less than 2 nM and preferably less than 1 nM.

The class of orally active, long acting, CNS-penetrant NK-1 receptor antagonists of use in the present invention is identified using a combination of the following assays:

ASSAY 1: NK-1 Receptor binding

NK-1 receptor binding assays are performed in intact Chinese hamster ovary (CHO) cells expressing the human NK-1 receptor using a modification of the assay conditions described by Cascieri et al, *J. Pharmacol. Exp. Ther.*, 1992, 42, 458. The receptor is expressed at a level of 3×10$^5$ receptors per cell. Cells are grown in monolayer culture, detached from the plate with enzyme-free dissociation solution (Speciality Media Inc.), and washed prior to use in the assay. $^{125}$I-Tyr$^8$-substance P (0.1 nM, 2000 Ci/mmol; New England Nuclear) is incubated in the presence or absence of test compounds (dissolved in 5 µl dimethylsulphoxide, DMSO) with 5×10$^4$ CHO cells. Ligand binding is performed in 0.25 ml of 50 mM Tris-HCl, pH7.5, containing 5 mM MnCl$_2$, 150 mM NaCl, 0.02% bovine serum albumin (Sigma), 50 µg/ml chymostatin (Peninsula), 0.1 nM phenylmethylsulphonyl fluoride, 2 µg/ml pepstatin, 2 µg/ml leupeptin and 2.8 µg/ml furoyl saccharine. The incubation proceeds at room temperature until equilibrium is achieved (>40 minutes) and the receptor-ligand complex is harvested by filtration over GF/C filters pre-soaked in 0.1% polyethylenimine using a Tomtek 96-well harvester. Non-specific binding is determined using excess substance P (1 µM) and represents <10% of total binding.

ASSAY 2: Gerbil Foot-Tapping

CNS-penetrant NK-1 receptor antagonists for use in the present invention can be identified by their ability to inhibit foot tapping in gerbils induced by anxiogenic agents (such as pentagastrin) or central infusion of NK-1 receptor agonists such as GR73632, or caused by aversive stimulation such as foot shock or single housing, based on the method of Rupniak & Williams, *Eur. J. Pharmacol.*, 1994, 265, 179.

Briefly, male or female Mongolian gerbils (35–70 g) are anaesthetised by inhalation of an isoflurane/oxygen mixture to permit exposure of the jugular vein in order to permit administration of test compounds or vehicle in an injection volume of 5 ml/kg i.v. Alternatively, test compounds may be administered orally or by subcutaneous or intraperitoneal routes. A skin incision is then made in the midline of the scalp to expose the skull. An anxiogenic agent (e.g. pentagastrin) or a selective NK-1 receptor agonist (e.g. GR73632 (d Ala[L-Pro$^9$,Me-Leu$^{10}$]-substance P-(7-11)) is infused directly into the cerebral ventricles (e.g. 3 pmol in 5 µl i.c.v., depending on test substance) by vertical insertion of a cuffed 27 gauge needle to a depth of 4.5 mm below bregma. The scalp incision is closed and the animal allowed to recover from anaesthesia in a clear perspex observation box (25 cm×20 cm×20 cm). The duration of hind foot tapping is then recorded continuously for approximately 5 minutes. Alternatively, the ability of test compounds to inhibit foot tapping evoked by aversive stimulation, such as foot shock or single housing, may be studied using a similar method of quantification.

ASSAY 3: Ferret Emesis

Individually housed male ferrets (1.0–2.5 kg) are dosed orally by gavage with test compound. Ten minutes later they are fed with approximately 100 g of tinned cat food. At 60 minutes following oral dosing, cisplatin (10 mg/kg) is given i.v. via a jugular vein catheter inserted under a brief period of halothane anaesthesia. The catheter is then removed, the jugular vein ligated and the skin incision closed. The ferrets recover rapidly from the anaesthetic and are mobile within 10–20 minutes. The animals are observed continuously during recovery from the anaesthetic and for 4 hours following the cisplatin injection. The numbers of retches and vomits occurring during the 4 hours after cisplatin administration are recorded by trained observers.

ASSAY 4: Separation-Induced Vocalisation

Male and female guinea-pigs pups are housed in family groups with their mothers and littermates throughout the study. Experiments are commenced after weaning when the pups are 2 weeks old. Before entering an experiment, the pups are screened to ensure that a vigorous vocalisation response is reproducibly elicited following maternal separation. The pups are placed individually in an observation cage (55 cm×39 cm×19 cm) in a room physically isolated from the home cage for 15 minutes and the duration of vocalisation during this baseline period is recorded. Only animals which vocahse for longer than 5 minutes are employed for drug challenge studies (approximately 50% of available pups may fail to reach this criterion). On test days each pup receives an oral dose or an s.c. or i.p. injection of test compound or vehicle and is then immediately returned to the home cage with its mother and siblings for 30 to 60 minutes before social isolation for 15 minutes as described above. The duration of vocalisation on drug treatment days is expressed as a percentage of the pre-treatment baseline value for each animal. The same subjects are retested once weekly for up to 6 weeks. Between 6 and 8 animals receive each test compound.

As used herein, the term "CNS-penetrant" refers to NK-1 receptor antagonists which are able to inhibit NK-1 receptor antagonist-induced foot-tapping in the gerbil as hereinafter defined.

Essentially, hind foot-tapping in the gerbil induced by infusion of the NK-1 receptor agonist, GR73632 (d Ala[L-Pro$^9$,Me-Leu$^{10}$]-substance P-(7-11)), under anaesthesia, directly into the central ventricles is inhibited when a CNS-penetrant NK-1 receptor antagonist is administered intravenously immediately prior to GR73632 challenge, wherein hind foot-tapping over a period of five minutes following recovery from the anaesthesia is inhibited with an ID$_{50}$≦3 mg/kg, and preferably with an ID$_{50}$≦1 mg/kg.

In an alternative method, the NK-1 receptor antagonist is administered orally, 1 hour prior to GR73632 challenge, wherein the foot-tapping over a period of five minutes following recovery from anaesthesia is inhibited with an ID$_{50}$≦30 mg/kg, and preferably with an ID$_{50}$≦10 mg/kg.

CNS-penetrant NK-1 receptor antagonists of use in the present invention are also effective in the attenuation of separation-induced vocalisations by guinea-pig pups as hereinafter defined.

Essentially, a vocalisation response in guinea-pig pups is induced by isolation from their mothers and littermates, which response is attenuated when a CNS-penetrant NK-1 receptor antagonist is administered subcutaneously 30 minutes prior to isolation, wherein vocalisations during the first 15 minutes of isolation are attenuated with an $ID_{50} \leq 20$ mg/kg, preferably with an $ID_{50} \leq 10$ mg/kg, and especially with an $ID_{50} \leq 5$ mg/kg.

In an alternative method, the NK-1 receptor antagonist is administered orally, 4 hours prior to isolation, wherein vocalisations during the first 15 minutes of isolation are attenuated with an $ID_{50} \leq 20$ mg/kg, preferably with an $ID_{50} \leq 10$ mg/kg, and especially with an $ID_{50} \leq 5$ mg/kg.

A suitable selection cascade for $NK_1$ antagonists of use according to the present invention is as follows:

(i) Determine affinity for human $NK_1$ receptor in radioligand binding studies (Assay 1); select compounds with $IC_{50} \leq 10$ nM, preferably $IC_{50} \leq 2$ nM, especially $IC_{50} \leq 1$ nM.

(ii) Determine ability of compounds to penetrate CNS by their ability to inhibit foot tapping in gerbils induced by central injection of an $NK_1$ agonist (Assay 2); select compounds that inhibit foot tapping with $ID_{50} \leq 3$ mg/kg i.v., and preferably $ID_{50} \leq 1$ mg/kg i.v. when administered immediately prior to central $NK_1$ agonist challenge, or $ID_{50} \leq 30$ mg/kg p.o., and preferably $ID_{50} \leq 10$ mg/kg p.o. 1 hour prior to challenge.

(iii) Determine central duration of action of compounds in gerbil foot tapping assay following intravenous administration 24 hours prior to central $NK_1$ agonist challenge; select compounds showing $\leq 25$-fold loss of potency compared with $ID_{50}$ determined in step (ii) above with the proviso that $ID_{50} \leq 10$ mg/kg i.v., and preferably $\leq 5$ mg/kg i.v. after 24 hour pre-treatment.

(iv) Determine oral bioavailability of compounds by pharmacokinetic analysis, activity in gerbil foot tapping assay following oral administration and/or by ability to inhibit cisplatin-induced emesis in ferrets (Assay 3); select compounds with $ID_{90} \leq 3$ mg/kg p.o., and preferably $ID_{90} \leq 1$ mg/kg p.o.

Particularly preferred compounds of use in the present invention are identified using steps (i) to (iv) followed by step (v):

(v) Determine activity of compounds in assays sensitive to conventional anxiolytic drugs (inhibition of pharmacologically evoked foot tapping in gerbils and/or inhibition of distress vocalisations in guinea-pig pups (Assay 4)). Select compounds with $ID_{50} \leq 20$ mg/kg, and preferably $ID_{50} \leq 10$ mg/kg.

Yet further preferred compounds of use in the present invention may be selected from those compounds which satisfy the NK-1 receptor binding criteria of step (i) which, in addition, have $\leq 5$-fold shift in affinity when incubated in the presence of human serum albumin (HSA) to show non-specific protein binding.

One example of a NK-1 receptor antagonist of use in the present invention is the compound 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, the preparation of which is described in International Patent Specification No. WO 95/16679. In the aforementioned assays, this compound has the following activity:

human NK-1 receptor binding: $IC_{50}=0.1$ nM
gerbil foot-tapping (5 mins.): $ID_{50}=0.36$ mg/kg i.v.
gerbil foot-tapping (24 hrs.): $ID_{50}=0.33$ mg/kg i.v.
ferret emesis: $ID_{90}<3$ mg/kg p.o.

The following example illustrates pharmaceutical compositions according to the invention.

EXAMPLE 1

Tablets containing 50–300 mg of NK-1 Antagonist

|  | Amount mg | | |
|---|---|---|---|
| NK-1 antagonist | 50.0 | 100.0 | 300.0 |
| Microcrystalline cellulose | 80.0 | 80.0 | 80.0 |
| Modified food corn starch | 80.0 | 80.0 | 80.0 |
| Lactose | 189.5 | 139.5 | 139.5 |
| Magnesium Stearate | 0.5 | 0.5 | 0.5 |

The active ingredient, cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 50 mg, 100 mg and 300 mg of the NK-1 receptor antagonist per tablet.

We claim:

1. A method for the treatment or prevention of a substance use disorder, which method comprises the oral administration to a patient in need thereof of an effective amount of an orally active, CNS-penetrant NK-1 receptor antagonist wherein the NK-1 receptor antagonist is long acting as determined by its ability to inhibit NK-1 receptor agonist-induced foot-tapping in the gerbil with an $ID_{50}$ less than or equal to 10 mg/kg i.v. after 24 hour pre-treatment.

2. A method according to claim 1 wherein the NK-1 receptor antagonist is:

2-(S)-(3,5-bis(trifluoromethyl)benzyloxy)-3(S)-(4-fluorophenyl)-4-(3-(5-oxo-1H,4H-1,2,4-triazolo)methyl)morpholine;

2-(R)-(1-(R)-(3,5-bis(trifluoromethyl)phenyl)ethoxy)-4-(3-(5-oxo-1H,4H-1,2,4-triazolo)methyl)-3-(S)-phenylmorpholine;

2-(S)-(3,5-bis(trifluoromethyl)benzyloxy)-4-(3-(5-oxo-1H,4H-1,2,4-triazolo)methyl)-3-(S)-phenylmorpholine;

2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine;

2-(R)-(1-(R)-(3,5-bis(trifluoromethyl)phenyl)ethoxy)-4-(5-(N,N-dimethylamino)methyl-1,2,3-triazol-4-yl)methyl-3-(S)-phenylmorpholine;

2-(R)-(1-(R)-(3,5-bis(trifluoromethyl)phenyl)ethoxy)-4-(5-(N,N-dimethylamino)methyl-1,2,3-triazol-4-yl)methyl-3-(S)-(4-fluorophenyl)morpholine;

2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine;

2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine;

2-(R)-(1-(R)-(3,5-bis(trifluoromethyl)phenyl)ethoxy)-4-(4-N,N-dimethylaminobut-2-yn-yl)-3-(S)-(4-fluorophenyl)morpholine;

(3S,5R,6S)-3-[2-cyclopropoxy-5-(trifluoromethoxy)phenyl-1-oxa-7-aza-spiro[4.5]decane;

(3R,5R,6S)-3-[2-cyclopropoxy-5-(trifluoromethoxy)phenyl-1-oxa-7-aza-spiro[4.5]decane;

(±)-(2R3R,2S3S)-N-{[2-cyclopropoxy-5-(trifluoromethoxy)phenyl]methyl}-2-phenylpiperidin-3-amine;

or a pharmaceutically acceptable salt thereof.

3. A method according to claim 1 wherein the substance use disorders are substance dependence or abuse with or without physiological dependence.

4. A method according to claim 1 wherein the substance associated with the disorders is selected from: alcohol, amphetamines or amphetamine-like substances, caffeine, cannabis, cocaine, hallucinogens, inhalants, nicotine, opioids, phencyclidine or phencyclidine-like compounds, sedative-hypnotics or benzodiazepines, and combinations of the above.

5. A method according to claim 1 wherein the substance use disorders are selected from drug withdrawal disorders; alcohol withdrawal delirium; amphetamine withdrawal; cocaine withdrawal; nicotine withdrawal; opioid withdrawal; sedative, hypnotic or anxiolytic withdrawal with or without peripheral disturbances; sedative, hypnotic or anxiolytic withdrawal delirium; and withdrawal symptoms due to addictive substances.

6. A method according to claim 1 wherein the substance use disorders are selected from substance-induced anxiety disorder with onset during withdrawal; substance-induced mood disorder with onset during withdrawal; and substance-induced sleep disorder with onset during withdrawal.

* * * * *